United States Patent [19]

Uchiyama

[11] Patent Number: 4,896,023
[45] Date of Patent: Jan. 23, 1990

[54] DRY AND WET HEATER

[76] Inventor: Goro Uchiyama, 832-10, Oaza-Suna, Kawagoe-Shi, Saitama-Ken, Japan

[21] Appl. No.: 199,251

[22] Filed: May 26, 1988

[30] Foreign Application Priority Data

Dec. 21, 1987 [JP] Japan .............................. 62-193886[U]

[51] Int. Cl.⁴ .............................................. H05B 1/00
[52] U.S. Cl. ...................................... 219/521; 219/242
[58] Field of Search ................ 219/242, 521, 385, 436, 219/438, 439

[56] References Cited

U.S. PATENT DOCUMENTS

| 1,464,255 | 8/1923 | Zimmermann | 219/239 |
| 1,694,725 | 12/1928 | Tabb | 219/521 |
| 1,809,510 | 6/1931 | Churchill | 219/242 |
| 2,262,506 | 11/1941 | Levandowski | 219/242 |
| 2,907,861 | 10/1959 | Melton | 219/521 |
| 3,222,499 | 12/1965 | Conlin et al. | 219/436 |
| 4,121,091 | 10/1978 | Wareham | 219/521 |
| 4,504,733 | 3/1985 | Walsh | 219/521 |

FOREIGN PATENT DOCUMENTS 494284 10/1938 United Kingdom .

Primary Examiner—A. D. Pellinen
Assistant Examiner—Geoffrey Evans
Attorney, Agent, or Firm—Fleit, Jacobson, Cohn, Price, Holman & Stern

[57] ABSTRACT

A heater which has a heating chamber of vessel shape of liquidtight structure for containing an article to be heated and a heater provided at the center of the heating chamber for heating the article to be heated directly or indirectly through a solid heat medium or a heating liquid.

3 Claims, 2 Drawing Sheets

DRY AND WET HEATER

FIELD OF THE INVENTION

This invention relates to a dry and wet heater for use in thermal sterilization of a medical implement, preliminary heating of component to be plated or other heating at low to high temperatures.

DESCRIPTION OF THE PRIOR ART

A heater for special use in heating in a range of 100° C. or lower to approx. 200° C. is known, such as a wet heating with steam or a dry heating by electric heating. The dry heating heretofore employs a tray-shaped heater to be specified at its heating position and has a disadvantage that the heating is used exclusively for dry heating with less availability. Further, a heater adapted for both dry and wet is not known.

SUMMARY OF THE INVENTION

An object of this invention is to provide a dry and wet heater which can heat by dry and wet heating type with uniform heating distribution, high thermal efficiency, working without disturbance even at high temperature in its heating section to be used and good availability.

The above object of the invention can be achieved by a dry and wet heater comprising a cartridge type rod-like heater 3 provided at the center of a vessel-like heating chamber 2 provided in a body 1 from the side wall of the chamber, a porous cap mechanism 4 detachably provided a the port of the heating chamber 2 for stably containing an article to be heated in the heating chamber 2 to control heat dissipation externally, and a contact preventive protector 5 provided on the outer periphery of the port of the heating chamber 2.

In the heater of this invention, when a power source is turned ON and a temperature is set, the rod-like heater 3 is heated to form a heating section having a cylindrical heating distribution in the whole working space 7 of the heating chamber 2 at the heater 3 as a center. This heat is reflected on the inner wall and the bottom of the chamber and the cap mechanism 4 to be uniformized, and even if an article W to be heated is placed at any of the working space 7, it is uniformly and efficiently heated. The article W to be heated is set in the heating chamber 2 from the through hole 8 of the cap mechanism 4, and heated at necessary temperature. In case of dry heating, heat medium H, such as silicon particles, glass particles or ceramic particles can be used. Liquid, such as water can be also used as the heat medium in case of wet heating.

According to this invention, the article W to be heated can be uniformly heated even at any in the heating chamber 2 with high thermal efficiency to be of both dry and wet types. Since the working port is protected by the protector 5, there is no danger of a burn.

According to this invention, the control of heat dissipation to an exterior and the support of the article W to be heated can be carried out by the cap mechanism 4. Therefore, the heater has such advantages that the article W to be heated can be supported without reducing its thermal efficiency, and various heating works, such as high temperature heating sterilization of a medical implement and low temperature heating of component to be plated from low to high temperature can be utilized.

DESCRIPTION OF THE PREFERRED EMBODIMENTS

Figure 1:
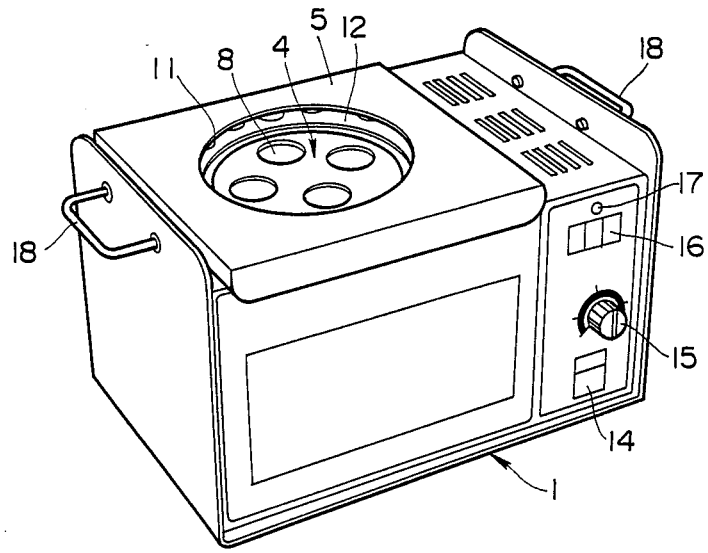
FIG. 1 is a perspective view of an embodiment of a dry and wet heater according to the present invention.
Figure 2:
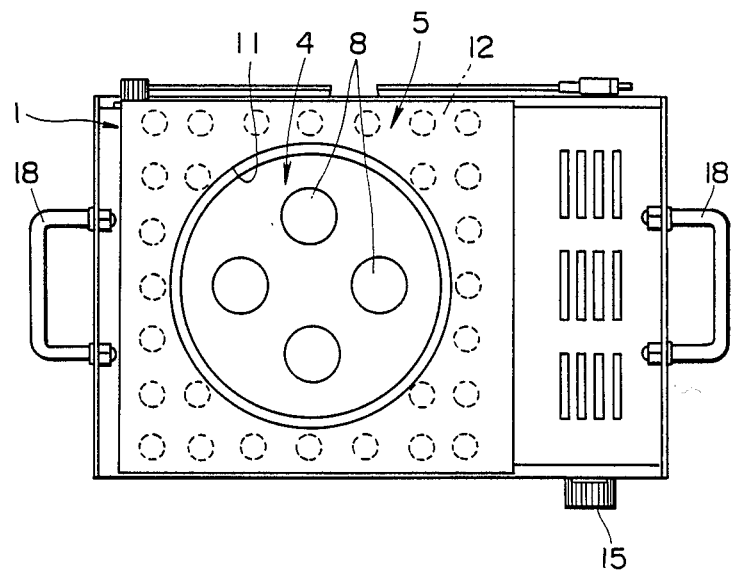
FIG. 2 is a plan view of the embodiment.
Figure 3:
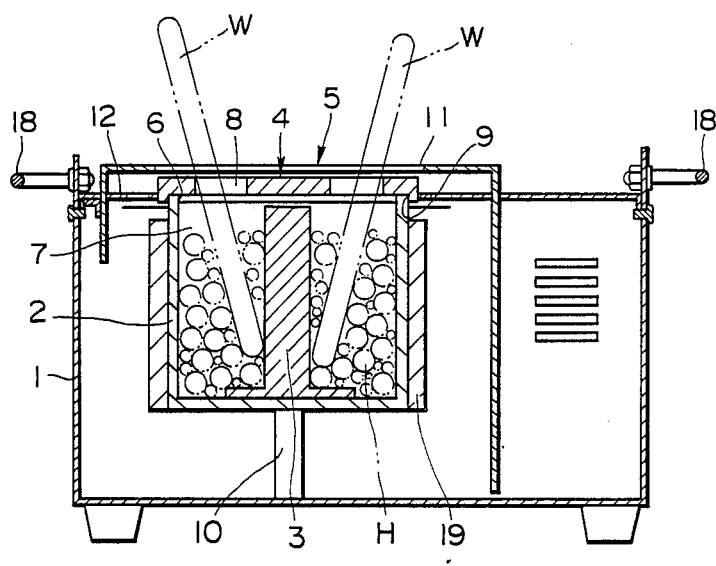
FIG. 3 is a longitudinal sectional view of the embodiment.

The invention will be described with respect to an embodiment of a dry and wet heater with reference to the accompanying drawings.

A heating chamber 2 has a cylindrical vessel shape opened at one side surface, an opening 6 is utilized for a working port, the other side wall is used as a mount of a rod-like heater 3, liquidtightly formed of metal, ceramics or other refractory material, and fixedly mounted at a body 1 with the opening 6 disposed upward.

The heater 3 is of a cartridge type, stood upward at the center on the bottom of the heating chamber 2 in a rod shape having substantially the same height as the chamber 2 or slightly lower than the height of the chamber 2 to form a doughnut-shaped working space 7 to the inner wall of the chamber.

A cap mechanism 4 blocks the opening 6 of the vessel-like heating chamber 2 to function as a cover for suppressing the heat dissipation to an exterior, to simultaneously control the heat dissipation by one or more through holes 8 formed thereat, and to support an article W to be heated by the through holes 8. The cap mechanism 4 is formed of a thick metal plate, ceramics or other refractory material, and has engaging means 9 for engaging with the outer periphery of the opening of the heating chamber 2. Reference numeral 10 designates a mounting leg for eliminating the thermal influence of the heating chamber 2 by separating the heating chamber 2 from the bottom of the body 1.

A protector 5 protects fingers of a worker against the high temperature of the heating chamber 2. When the cap mechanism 4 is mounted in the heating chamber 2, it has a working port 11 opened to surround the cap mechanism 4 at slightly outside and upper position therefrom, is formed of a refractory material, and mounted thermally-independently from the structure on the body 1. Further, a porous spacer 12 is provided on the periphery of the opening 6 to interrupt the heat transfer to the protector 5, and outer boards.

In case of dry heating, silicone resin particles, glass particles or ceramic particles are filled in the heating chamber 2 as heat medium H, while in case of wet heating, water or other liquid is used as heat medium. Reference numeral 14 designates a power switch, numeral 15 denotes a temperature setting dial, numeral 16 is a digital temperature indicator (which may be of analog type), numeral 17 is a setting temperature display lamp, numeral 18 is a grip, and numeral 19 is a heat insulator.

What is claimed is:

1. A heater for heating articles by conduction with a liquid or solid heating medium, the heater comprising a housing, a heating vessel with an open top supported in the housing, the vessel having a base wall and a peripheral wall defining a heating chamber for containing the heating medium, a rod-like heating element extending upwardly into the chamber from the base wall, a cap covering the open top of the vessel, the cap having apertures for inserting articles to be heated into the heating chamber at locations surrounding the heating element, a perforated spacer plate surrounding the top of the vessel, and a protector supported on said plated of inhibiting user contact with the cap, the protector having an upper wall spaced above the cap and providing a central opening for obtaining access to said apertures, the perforated plated interrupting heat transfer from the vessel to the protector.

2. A heater as claimed in claim 1 wherein the opening is dimensioned substantially to correspond with outer dimensions of the cap.

3. A heater as defined in claim 1 wherein the housing has a bottom wall with an upstanding leg, and the heating vessel is supported on the leg above the bottom wall.

* * * * *